United States Patent
Chiang et al.

(10) Patent No.: US 8,137,296 B2
(45) Date of Patent: Mar. 20, 2012

(54) WRIST GUARD

(75) Inventors: Pang-Ching Chiang, Taipei (TW); Kuo-Wei Lee, Taipei (TW)

(73) Assignee: Plus Meditech Co., Ltd., Tainan (TW)

( * ) Notice: Subject to any disclaimer, the term of this patent is extended or adjusted under 35 U.S.C. 154(b) by 288 days.

(21) Appl. No.: 12/564,784

(22) Filed: Sep. 22, 2009

(65) Prior Publication Data
US 2010/0298750 A1 Nov. 25, 2010

(30) Foreign Application Priority Data
May 21, 2009 (TW) ................................ 98208867 U (51) Int. Cl.
*A61F 5/00* (2006.01)
*A61F 5/37* (2006.01)
*A63B 23/14* (2006.01)
*A41D 19/00* (2006.01)

(52) U.S. Cl. ................. 602/21; 128/878; 482/44; 2/162
(58) Field of Classification Search .......... 602/1, 20–22, 602/5–6, 12, 62, 64, 9; 128/878, 880; 482/44, 482/47–48
See application file for complete search history.

(56) References Cited

U.S. PATENT DOCUMENTS
4,510,928 A * 4/1985 Ackley ............................. 602/4
5,778,449 A * 7/1998 Oetting et al. ...................... 2/16
* cited by examiner

*Primary Examiner* — Patricia Bianco
*Assistant Examiner* — Tarla Patel
(74) *Attorney, Agent, or Firm* — WPAT, P.C.; Anthony King (57) ABSTRACT

A wrist guard has a glove body and two adjustable support parts. The glove body has a palm-holding part and two connection parts. The palm-holding part is mounted in an upper half portion of the glove body. The two connection parts are mounted to a lower half portion of the glove body and have a through hole respectively. The adjustable support parts are adjustably mounted to the corresponding connection part. Each of them has a support piece and a locking module. The support piece having an interconnection part is movably mounted to the corresponding connection part, and a locating slot is formed through the interconnection part to overlap with the through hole of the corresponding connection part. The locking module passes through the through hole of the corresponding connection part and locating slot to position the support piece on the corresponding connection part.

8 Claims, 9 Drawing Sheets

WRIST GUARD

BACKGROUND OF THE INVENTION

1. Field of the Invention

The present invention relates to a wrist guard, and more particularly to a medical wrist guard for fixing and protecting wrist.

2. Description of Related Art

Figure 8:
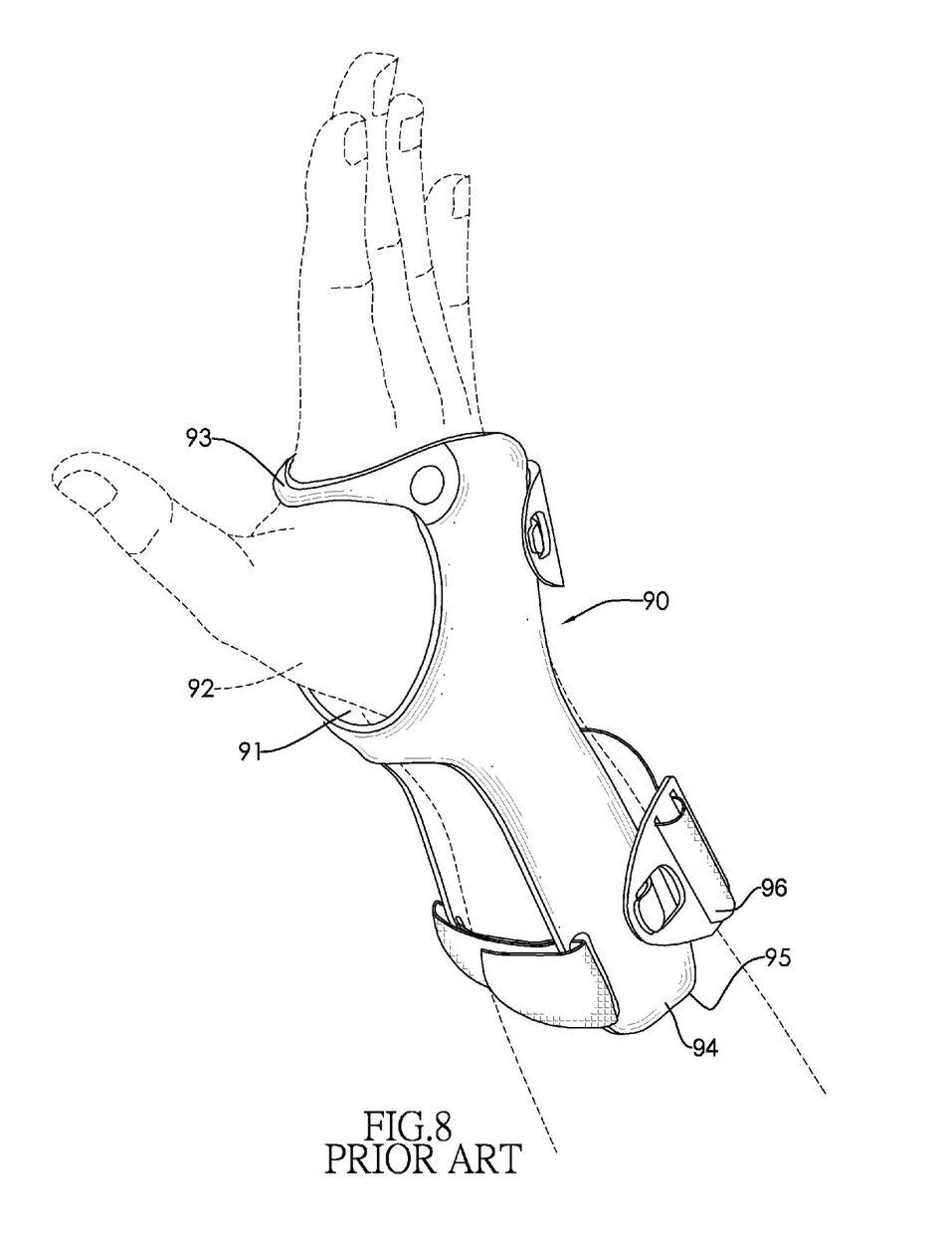
FIG. 8 is a perspective view of a conventional wrist guard in accordance with the prior art.

With reference to FIG. 8, a regular wrist guard is glove body on a user's wrist for the purpose of fixing, supporting and protecting wrist. A conventional wrist guard has a glove body (90) for wrapping around user's hand (92). Two exit holes (91) are formed in an upper half portion of the glove body (90), and a connection part (93) located between the two exit holes (91) is fixed with the glove body (90). The two exit holes (91) are provided for thumb and the rest of fingers to stick out and move freely, and the connection part (93) between the exit holes (91) sits on a place between the thumb and the index finger of the hand (92). Furthermore, two support parts (94) are extended out in a lower half portion of the glove body (90). A binding strap (96) is mounted on the two support parts (94) to define a hand insertion hole (95) for a hand to insert into. The two support parts (94) are bound and fastened on the user's hand (92) by the binding strap (96) when the user's hand is inserted into the hand insertion hole so as to support the wrist and mitigate the pressure that the wrist endures.

However, the support parts of the wrist guard are integrally formed on the glove body. As a result, when the wrist guard is used by users with different types of build, the length of the support part cannot be adjusted in response to the size of bone and the length of hand. This leads to limited support and protection given by the conventional wrist guard, giving rise to unexpected operational efficacy. Since the design of the support part in the conventional wrist guard fails to adjust length based on user's individual demand, the conventional wrist guard does not meet user's requirement and thus the utility is behind what is expected.

SUMMARY OF THE INVENTION

The main objective of the present invention is to provide a wrist guard for improving the shortcoming of the conventional wrist that fails to adjust a support length based on user's demand.

To achieve the foregoing main objective, a wrist guard addressed by the present invention has a glove body and two adjustable support parts.

The glove body has a palm-holding part and two connection parts. The palm-holding part is mounted in an upper half portion of the glove body. The two connection parts are mounted to a lower half portion of the glove body and have a through hole respectively.

The adjustable support parts are adjustably mounted to the corresponding connection part. Each of them has a support piece and a locking module. The support piece having an interconnection part is movably mounted to the corresponding connection part, and a locating slot is formed through the interconnection part to overlap with the through hole of the corresponding connection part. The locking module passes through the through hole of the corresponding connection part and locating slot to position the support piece on the corresponding connection part.

The wrist guard of the present invention allows user's hand to insert into and allows fingers to stick out the palm-holding part. The adjustable support parts are located at user's arm. User can first loosen the locking module to make the support pieces respectively move with respect to the connection parts, thereby allowing user to individually position the support piece after adjusting an adequate support length. The locking module is further tightened to fasten the support pieces on the connection parts so as to explore the maximum support and protection functionality of the wrist guard. As such, the design that the adjustable support part can be randomly adjusted and then fixed greatly enhances the utility of the wrist guard and addresses decent protection and pressure relief capability thereof.

Other objectives, advantages and novel features of the invention will become more apparent from the following detailed description when taken in conjunction with the accompanying drawings.

DETAILED DESCRIPTION OF THE PREFERRED EMBODIMENT

With reference to FIGS. 1 to 3 and FIG. 9, a wrist guard in accordance with a first preferred embodiment of the present invention has a glove body (10) and two adjustable support parts (20). The glove body (10) is a two-piece structure bound by multiple straps so as to envelop a hand therein. The glove body (10) has a palm-holding part (11) and two connection parts (12).

Figure 1:
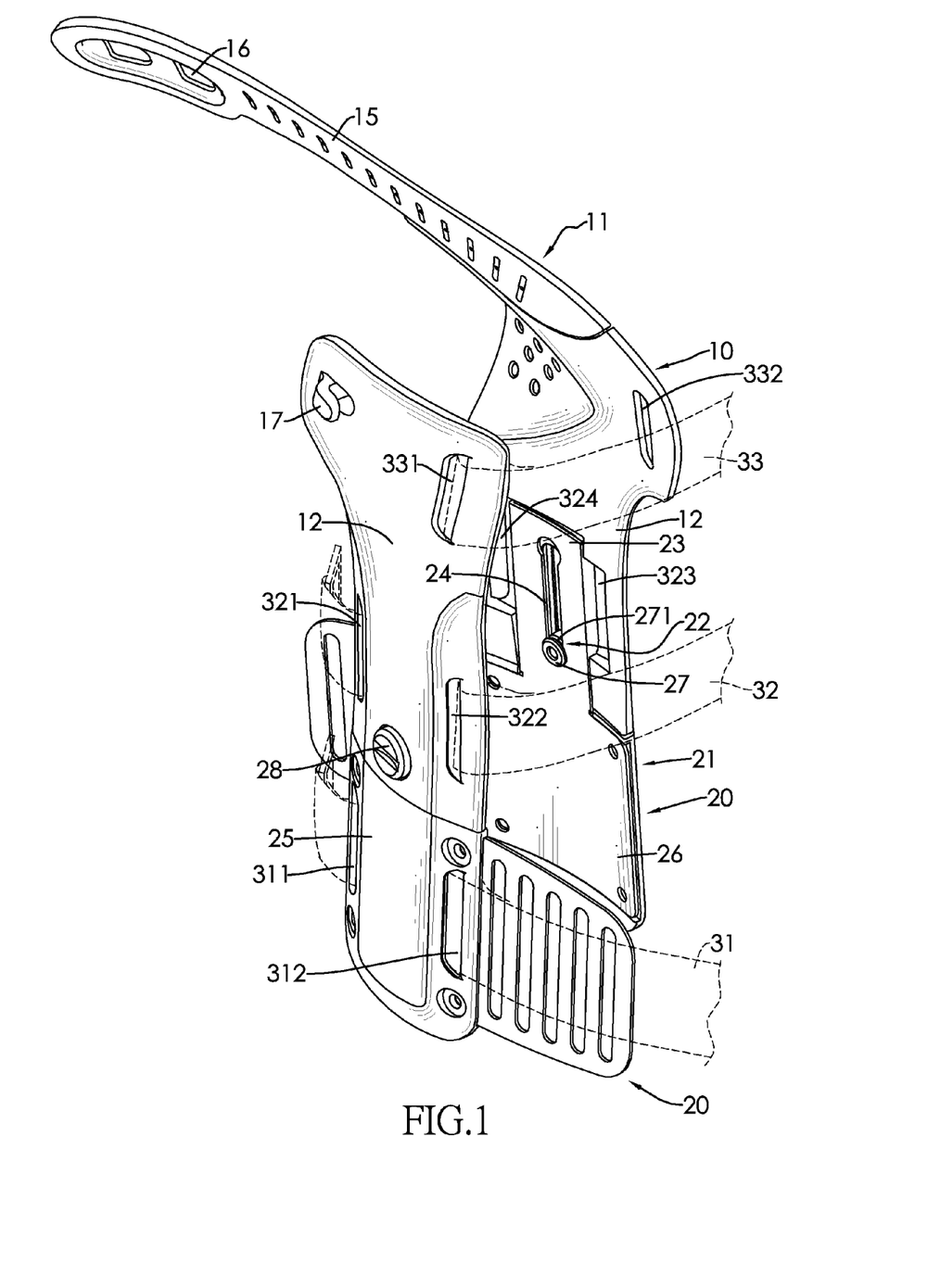
FIG. 1 is a perspective view of a first preferred embodiment of a wrist guard in accordance with the present invention.
Figure 2:
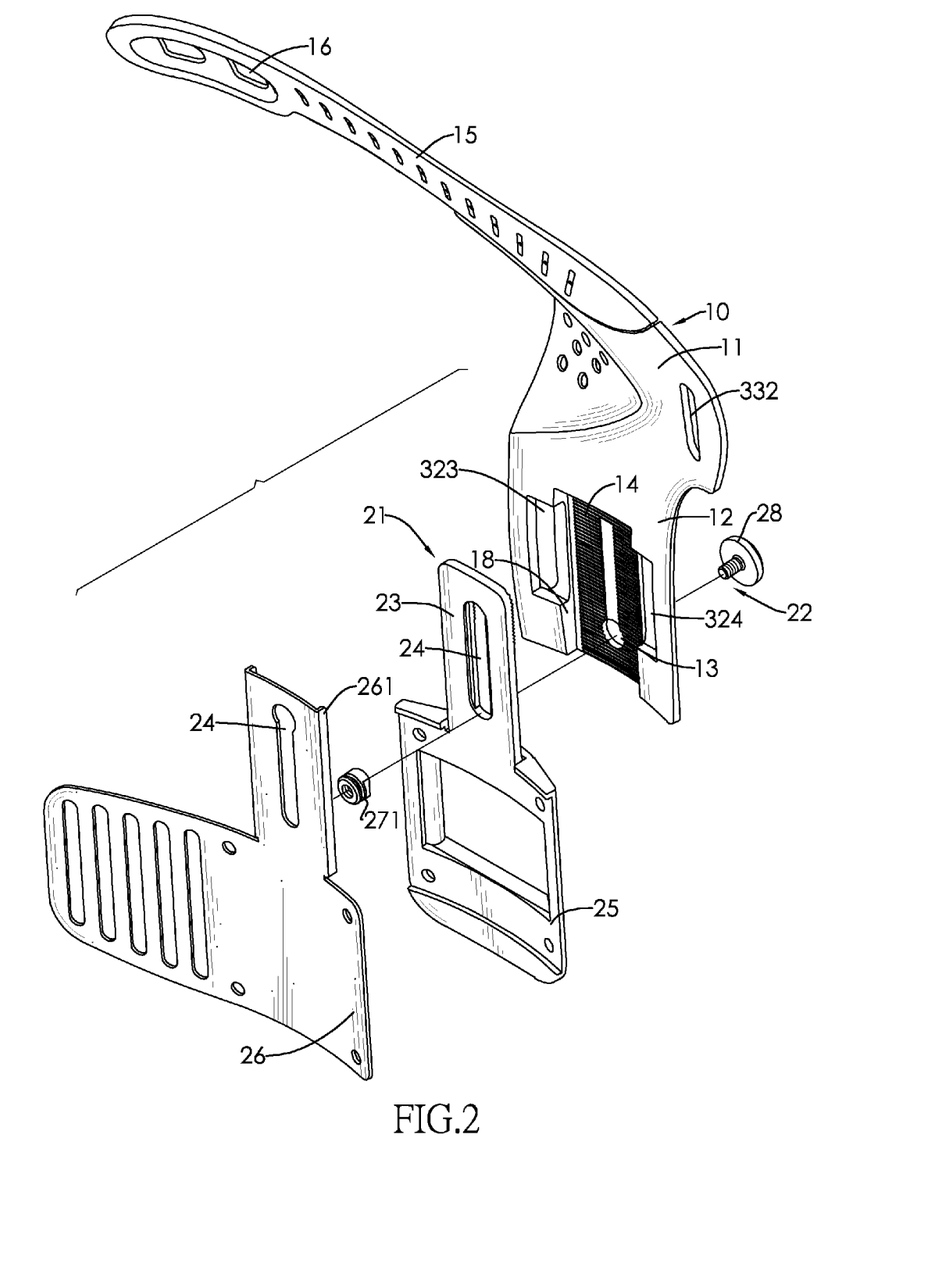
FIG. 2 is a partially exploded perspective view of the first preferred embodiment of the wrist guard in accordance with the present invention while viewing from one side of the wrist guard.
Figure 3:
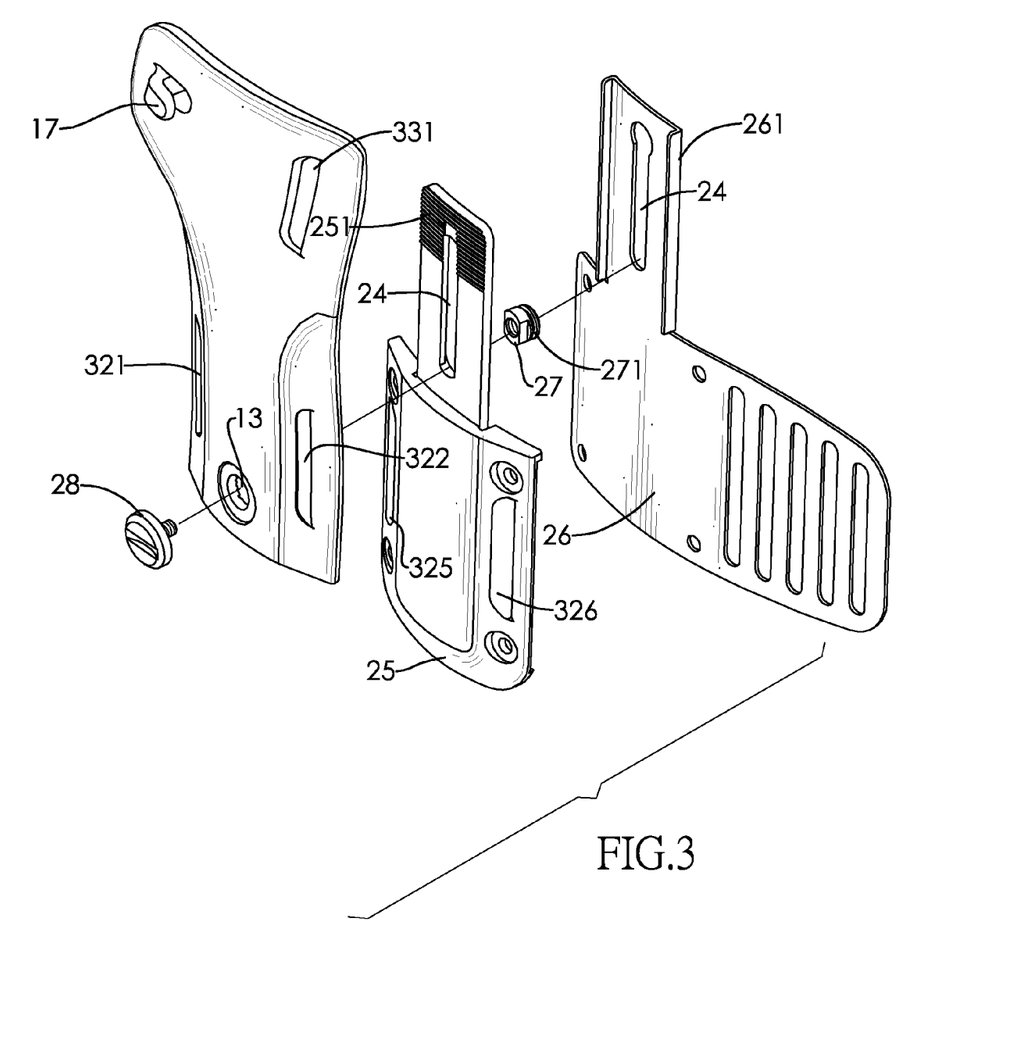
FIG. 3 is a partially exploded perspective view of the first preferred embodiment of the wrist guard in accordance with the present invention while viewing from another side of the wrist guard.

The palm-holding part (11) is formed on an upper half portion of the glove body (10) and has an adjustable belt (15) and a positioning button (17). The adjustable belt (15) is formed on and protrudes from a top of the palm-holding part (11), won't be easily deformed to lose its support capability and has a plurality of buttonholes (16) formed through the free end of the adjustable belt (15). The positioning button (17) is formed on the palm-holding part (11) to correspond to the adjustable belt (15) and can be buttoned into one of the buttonholes (16) so that a user can adjust in accordance with a palm size. Each connection part (12) is formed on a lower half portion of the glove body (10), and has a chamber (18)

and a through hole (13). The chamber (18) is concavely formed on an inner side of each of the two connection parts (12), and the through hole (13) penetrates through the chamber (18).

Each adjustable support part (20) is adjustably positioned and detachably mounted on one of the two connection parts (12) of the glove body (10), and has a support piece (21) and a locking module (22). The support piece (21) has an interconnection part (23) and a longitudinal locating slot (24). The interconnection part (23) is mounted on the support piece (21) to correspond to the connection part (12) and the is placed in the chamber (18). The longitudinal locating slot (24) is formed on the interconnection part (23) to overlap with the through hole (13). The locking module (22) is mounted in the through hole (13) and is inserted in the locating slot (24) for fastening the support piece (21) on a corresponding connection part (12).

Figure 6:
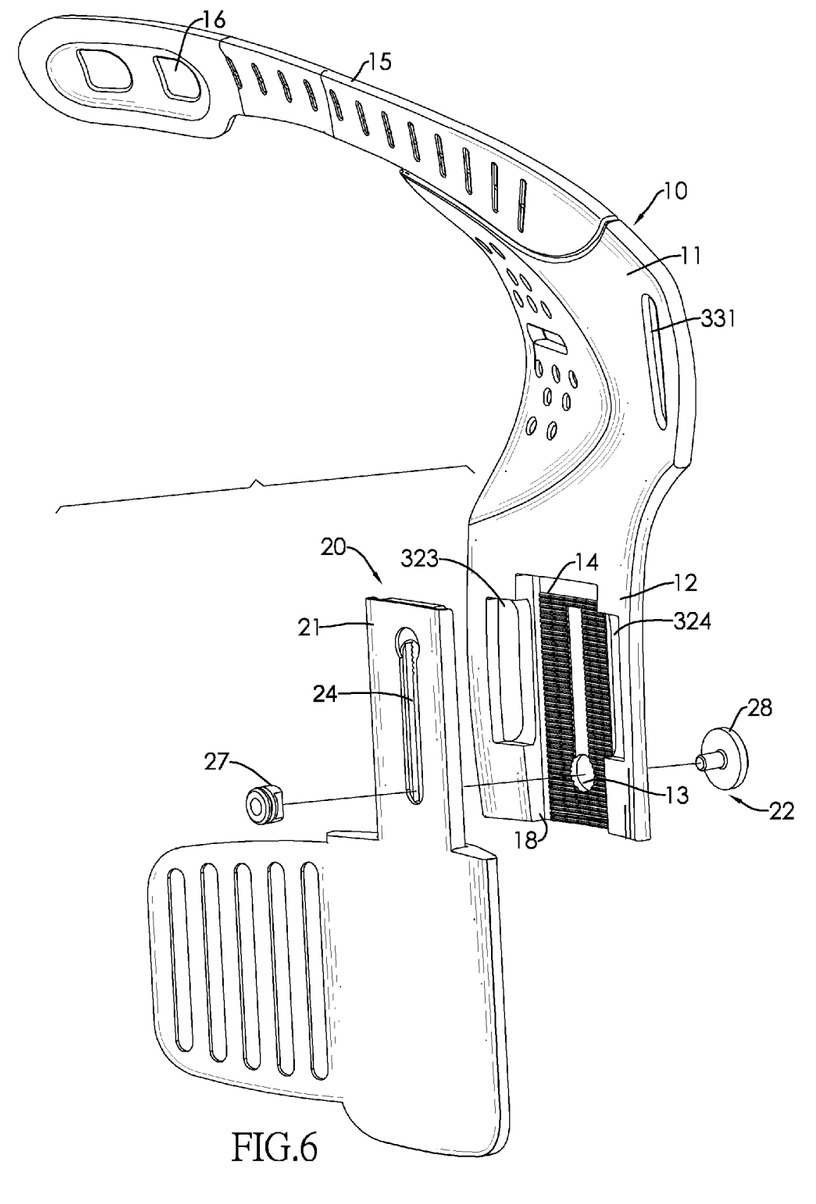
FIG. 6 is a partially exploded perspective view of a second preferred embodiment of the wrist guard in accordance with the present invention while viewing from one side of the wrist guard.
Figure 7:
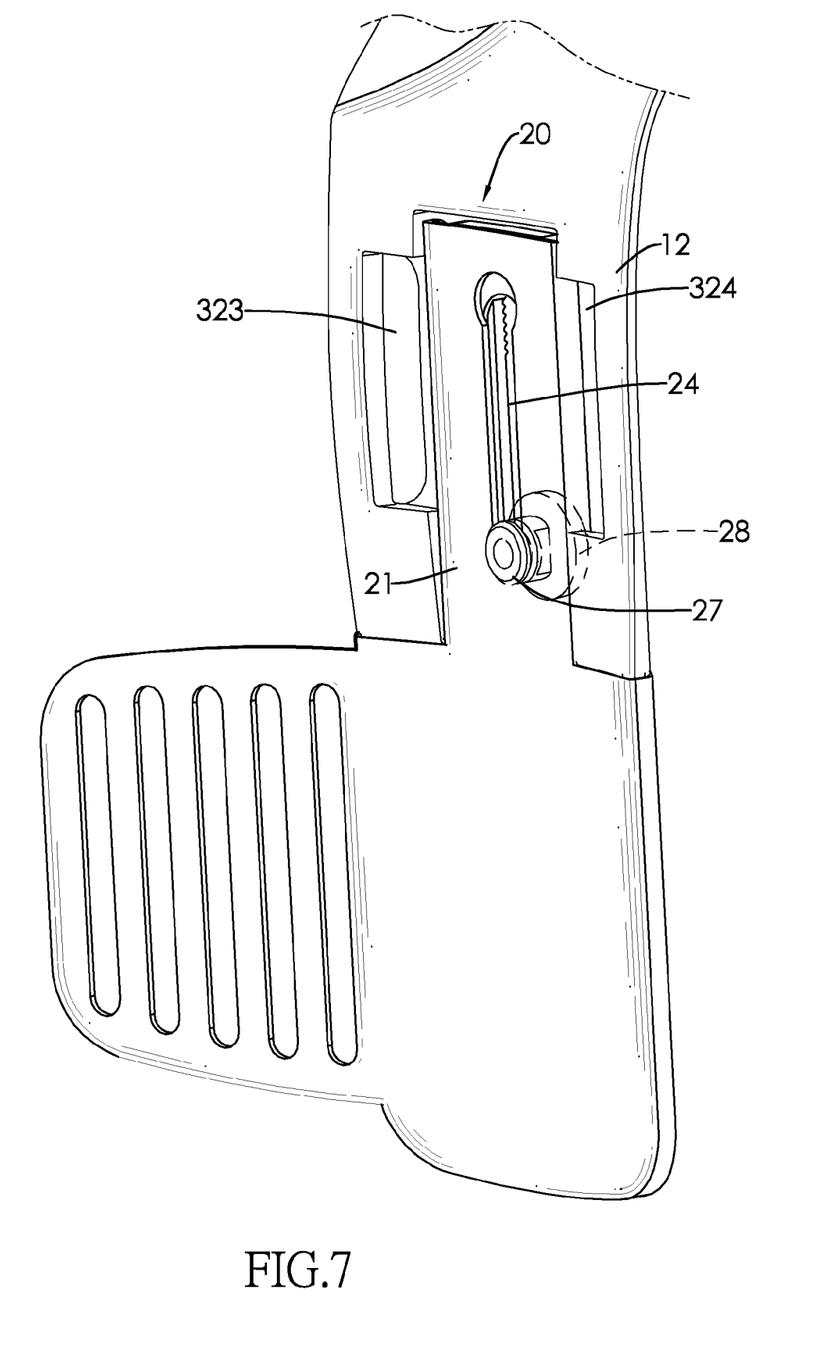
FIG. 7 is a partial perspective view of FIG. 6.

In the present embodiment, the support piece (21) may be an integrally formed part (with reference to FIG. 6 and FIG. 7). With further reference to FIG. 2 and FIG. 3, the support piece (21) further has an outer panel (25) and an inner panel (26). The inner panel (26) moves synchronously with the outer panel (25). The outer panel (25) is detachably mounted between the connection part (12) and the inner panel (26). A fin (261) urging against the outer panel (25) is formed on the inner panel (26). Therefore, while the inner panel (26) moves, the outer panel (25) simultaneously moves with the inner panel (26) for the purpose of synchronization. The longitudinal locating slot (24) is defined through the outer panel (25). The connection part (12) further has an adjustment portion (14) that is formed on an inner side of the chamber (18). A fine-tuning part (251) is formed on a side of the outer panel (25) abutting the adjustment portion (14) for engagement with the adjustment portion (14). Hence, when applying a force to move the outer panel (25), the fine-tuning part (251) can be moved in steps on the adjustment portion (14) to facilitate user's adjustment. The adjustment portion (14) and the fine-tuning part (251) may be teeth-shaped parts or parts that can mutually engage with each other to be displaced relatively.

Figure 4:
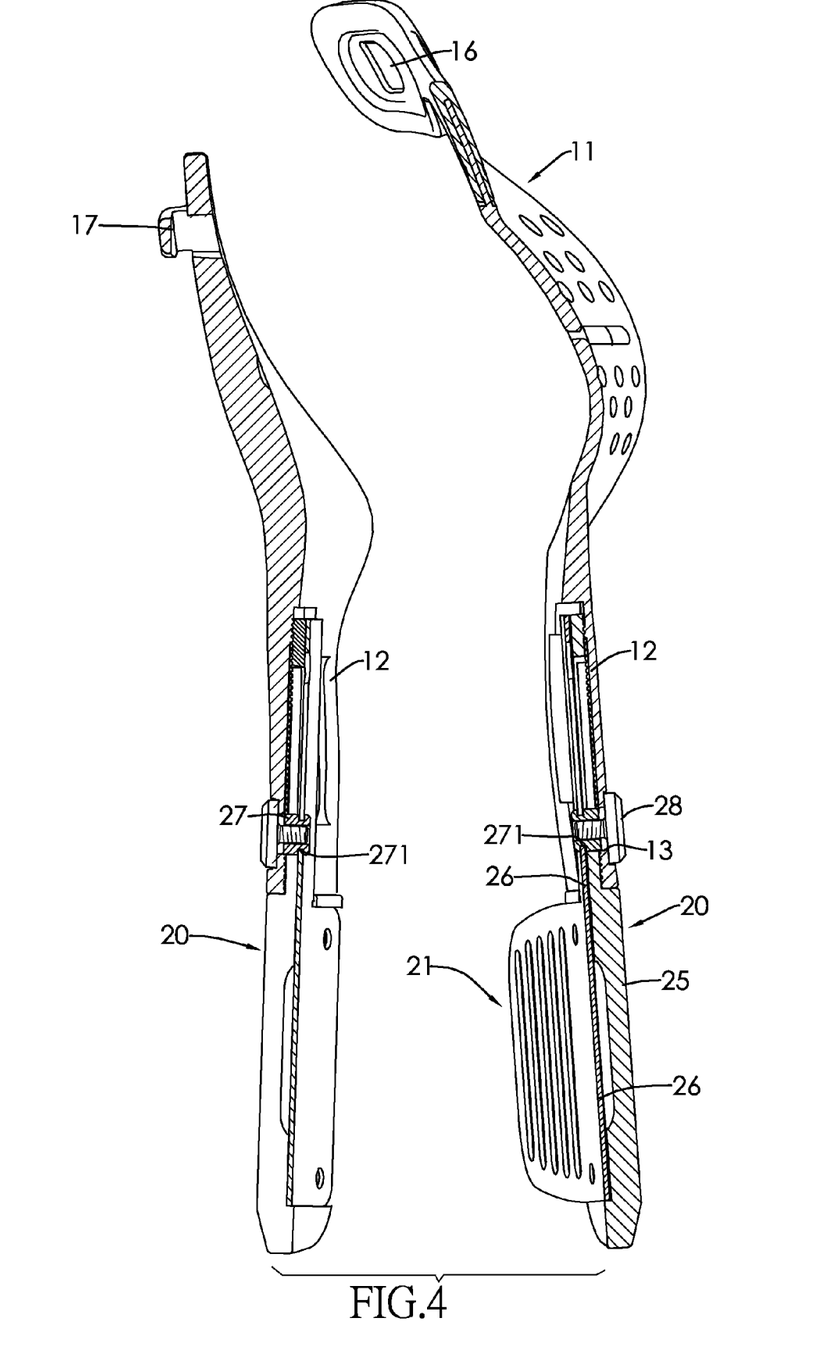
FIG. 4 is a cross-sectional view of the first preferred embodiment of the wrist guard without straps in accordance with the present invention.
Figure 5:
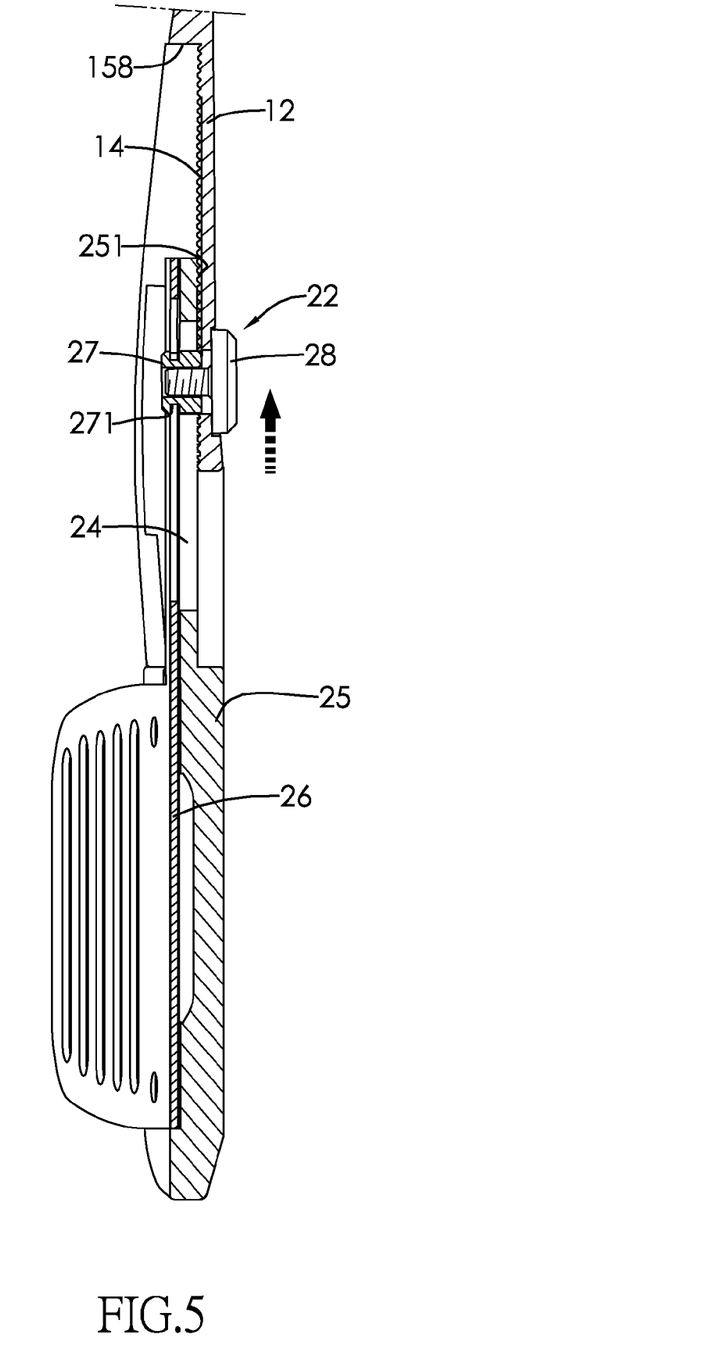
FIG. 5 is a partial cross-sectional view of the first preferred embodiment of the wrist guard in accordance with the present invention while moving part of the wrist guard.

With reference to FIG. 4 and FIG. 5, the locking module has a nut (27) and a bolt (28) that can be screwed with the nut (27). The nut (27) is located in the locating slot (24) and has a channel (271) serving to be engaged with the longitudinal locating slot (24) of the inner panel (26) and preventing the inner panel (26) from disengaging from the outer panel (25). The bolt (28) is inserted into the nut (27) through the through hole (13) and the longitudinal locating slot (24) of the outer panel (25). While being tightly screwed, the bolt (28) and the nut (27) fasten the support piece (21) on the connection part (12).

Figure 9:
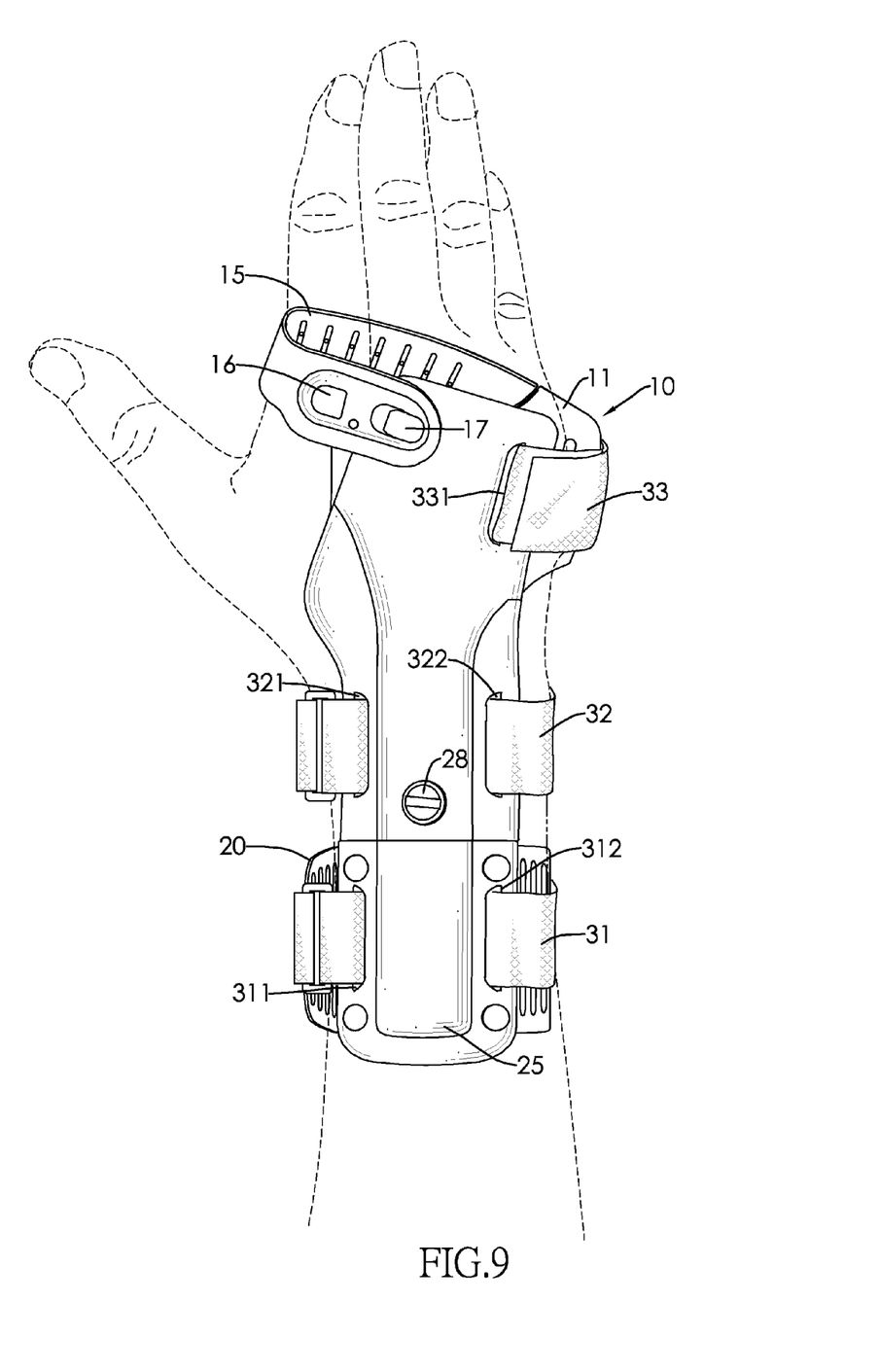
FIG. 9 is a perspective view of the first preferred embodiment of a wrist guard in accordance with the present invention when a user's hand is inserted therein.

As mentioned earlier, the glove body (10) is a two-piece structure, which needs to be bound by other straps so as to envelop a hand therein. With further reference to FIG. 1 and FIG. 9, two top long holes (331), (332) and four middle long holes (321), (322), (323), (324) are formed on the top portion, the bottom portion of the glove body (10) respectively. Further, four bottom long holes (311), (312), (313), (314) are formed on the two adjustable support parts (20). The two top long holes (331), (332) the four bottom long holes (311), (312), (313), (314) and four bottom long holes (311), (312), (313), (314) are penetrated through by a top strap (33), a middle strap (32) and a bottom strap (31) respectively. Once a user's hand slides into the wrist guard and the fingers stick out the palm-holding part (11), the length of the adjustable belt (15) is adequately adjusted in accordance with a palm size. The bolt (28) can be loosened first so that the support piece (21) can be smoothly moved to where the user can individually adjust the support piece (21) to provide sufficient support. The bolt (28) can be tightly screwed with the nut (27) to fix the support piece (21). At last the top strap (33), the middle strap (32) and the bottom strap (31) are fastened to tie up the glove body (10) and the adjustable support part (20) as a whole. Accordingly, the wrist guard can be attached on the wrist by adjusting those straps.

In sum, the support piece in the wrist guard of the present invention can be randomly adjusted a moving distance in response to user's demand and further enhances its utility to provide optimal support and achieve the functionality for pressure relief and protection. Besides, the design of the adjustable belt capable of adjusting length based on user's demand makes the use and adjustment of the wrist guard more humanized and delivers desired comfort and fixing support. As such, the adjustable design of the wrist guard enhances the utility, convenience and adaptability in operation and provides better functionality for support, pressure-relief, protection and so forth.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A wrist guard, comprising:
   a glove body having
      a palm-holding part mounted in an upper half portion thereof; and
      two connection parts formed on a lower half portion thereof, each having a through hole; and
   two adjustable support parts adjustably and detachably mounted on the respective connection parts, each having:
      a support piece having:
         an interconnection part movably mounted to a corresponding connection part; and
         a locating slot formed through the interconnection part to overlap with the through hole of the corresponding connection part;
         an outer panel and an inner panel assembled therewith, wherein the locating slot is defined through the outer panel and the inner panel; and
      a locking module passing through the through hole of the corresponding connection part and locating slot to position the support piece on the corresponding connection part, and having:
         a nut having a channel engaging the locating slot of the inner panel; and
         a bolt inserted in the through hole and the locating slot of the outer panel and screwed with the nut.

2. The wrist guard as claimed in claim 1, further comprising:
   an adjustment portion mounted on the connection part; and
   a fine-tuning part formed on a side of the corresponding outer panel abutting the adjustment portion, and longitudinally moved on the adjustment portion.

3. The wrist guard as claimed in claim 2, wherein the palm-holding part further comprises:
   an adjustable belt having a plurality of buttonholes; and
   a positioning button being opposite to the adjustable belt and buttoned into one of the buttonholes.

4. The wrist guard as claimed in claim 2, wherein the adjustment portion and the fine-tuning part are teeth-shaped.

5. The wrist guard as claimed in claim 4, wherein the palm-holding part further comprises:
   an adjustable belt having a plurality of buttonholes; and
   a positioning button being opposite to the adjustable belt and buttoned into one of the buttonholes.

6. The wrist guard as claimed in claim 4, wherein the glove body further comprises two top long holes, four middle long holes and the adjustable support part comprises four bottom long holes to be respectively penetrated through by a top strap, a middle strap and a bottom strap for binding the glove body and the adjustable support parts after a hand is inserted into the wrist guard.

7. The wrist guard as claimed in claim 6, wherein the palm-holding part further comprises:
   an adjustable belt having a plurality of buttonholes; and
   a positioning button being opposite to the adjustable belt and buttoned into one of the buttonholes.

8. The wrist guard as claimed in claim 1, wherein the palm-holding part further comprises:
   an adjustable belt having a plurality of buttonholes; and
   a positioning button being opposite to the adjustable belt and buttoned into one of the buttonholes.

* * * * *